United States Patent
Hawkes et al.

(10) Patent No.: US 9,749,900 B2
(45) Date of Patent: Aug. 29, 2017

(54) PATIENT MONITORING INVOLVING RECEIVING MULTIPLE ASYNCHRONOUS DATA STREAMS WITH ANTENNA DIVERSITY

(71) Applicant: KONINKLIJKE PHILIPS N.V., Eindhoven (NL)

(72) Inventors: Calvert Tazewell Hawkes, Sarasota, FL (US); Robert Andrew Harwell, Saint Cloud, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/911,475

(22) PCT Filed: Jul. 28, 2014

(86) PCT No.: PCT/IB2014/063469
§ 371 (c)(1),
(2) Date: Feb. 11, 2016

(87) PCT Pub. No.: WO2015/022594
PCT Pub. Date: Feb. 19, 2015

(65) Prior Publication Data
US 2016/0192234 A1  Jun. 30, 2016

Related U.S. Application Data

(60) Provisional application No. 61/866,181, filed on Aug. 15, 2013.

(51) Int. Cl.
*H04W 28/04* (2009.01)
*A61B 5/00* (2006.01)
(Continued)

(52) U.S. Cl.
CPC ........... *H04W 28/04* (2013.01); *A61B 5/0002* (2013.01); *G01R 33/3692* (2013.01);
(Continued)

(58) Field of Classification Search
CPC .... A61B 5/0002; A61B 5/055; G01R 33/283; G01R 33/3692; H04B 1/1081; H04W 28/04
(Continued)

(56) References Cited

U.S. PATENT DOCUMENTS 7,590,399 B2   9/2009   Shatara et al.
8,107,915 B2   1/2012   Bally et al.
(Continued)

FOREIGN PATENT DOCUMENTS

| WO | 2011/058458 | 5/2011 | |
| WO | WO 2011058458 A1 * | 5/2011 | ........... H04B 7/0602 |
| WO | 2012/095753 | 7/2012 | |

*Primary Examiner* — Hirdepal Singh

(57) ABSTRACT

A radio frequency (RF) receiving apparatus (10) includes a first and second omnidirectional RF antennas (20) at different spatial locations or orientations, a first and second RF receivers (24), each connected to a corresponding one of the first and second omnidirectional RF antennas (20), and a controller (32) connected to the first and second RF receivers (24). The first and second RF receivers (24) receive and demodulate RF signals of at least first and second carrier frequencies to recover data packets from at least a first device which transmits data packets on the first carrier frequency RF signal and a second device which transmits data packets on the second carrier frequency RF signal. The controller (32) is configured to control the RF receivers to cycle between receiving and demodulating the first carrier frequency RF signals concurrently to recover redundant data packets from the first device, and receiving and demodulating the second carrier frequency RF signals concurrently to recover redundant data packets from the second device. The (Continued)

Figure 1:
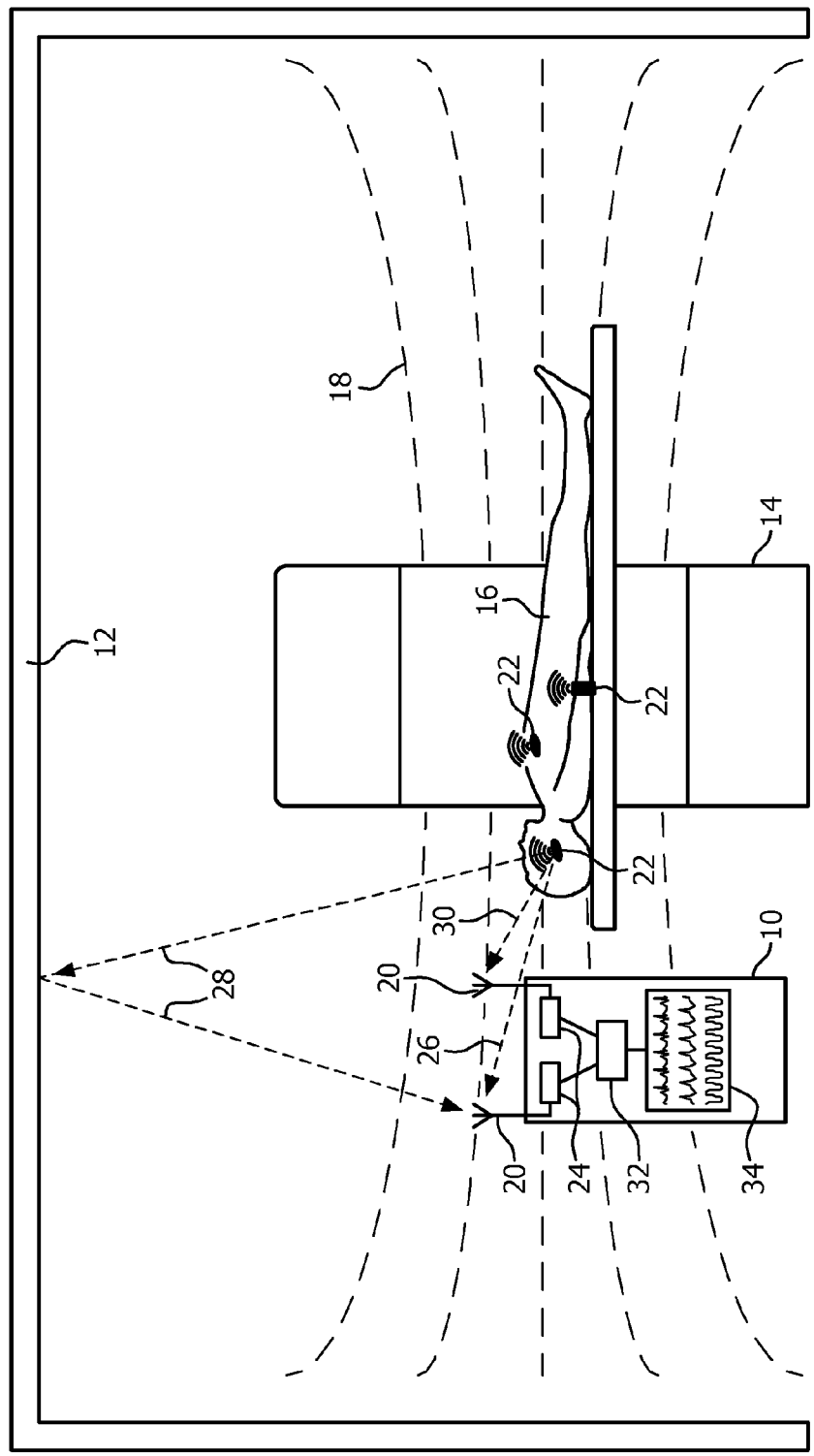

apparatus can be used to wirelessly transmit physiological patient monitoring data (e.g. an ECG signal) in the highly reflective environment of an MRI system.

13 Claims, 4 Drawing Sheets

(51) Int. Cl.
    *G01R 33/36*     (2006.01)
    *H04B 1/10*     (2006.01)
    *A61B 5/055*     (2006.01)
    *G01R 33/28*     (2006.01)

(52) U.S. Cl.
    CPC ............ *H04B 1/1081* (2013.01); *A61B 5/055* (2013.01); *G01R 33/283* (2013.01)

(58) Field of Classification Search
    USPC .................................................... 340/870.07
    See application file for complete search history.

(56) References Cited

U.S. PATENT DOCUMENTS

| | | | |
|---|---|---|---|
| 2004/0087282 A1 | 5/2004 | Ishikawa | |
| 2004/0229650 A1 | 11/2004 | Fitton et al. | |
| 2006/0017633 A1 | 1/2006 | Pronkine et al. | |
| 2006/0206024 A1* | 9/2006 | Weeks | A61B 5/0006 600/418 |
| 2009/0140739 A1* | 6/2009 | Bennett | G01R 33/3692 324/318 |
| 2010/0045480 A1* | 2/2010 | Vallapureddy | A61N 1/37223 340/870.28 |
| 2012/0215092 A1* | 8/2012 | Harris, III | H04B 7/0602 600/410 |
| 2014/0171783 A1* | 6/2014 | Schmidt | G01R 33/5673 600/413 |
| 2014/0275970 A1* | 9/2014 | Brown | G01R 33/3692 600/413 |
| 2015/0320342 A1* | 11/2015 | Biber | A61B 5/1128 600/411 |
| 2016/0021219 A1* | 1/2016 | Brown | A61B 6/541 370/216 |

* cited by examiner

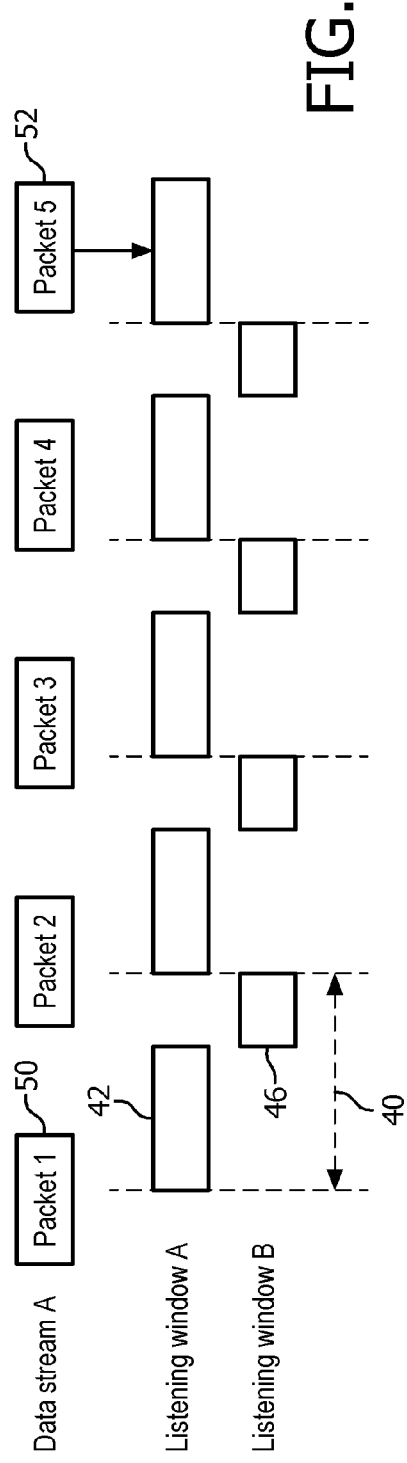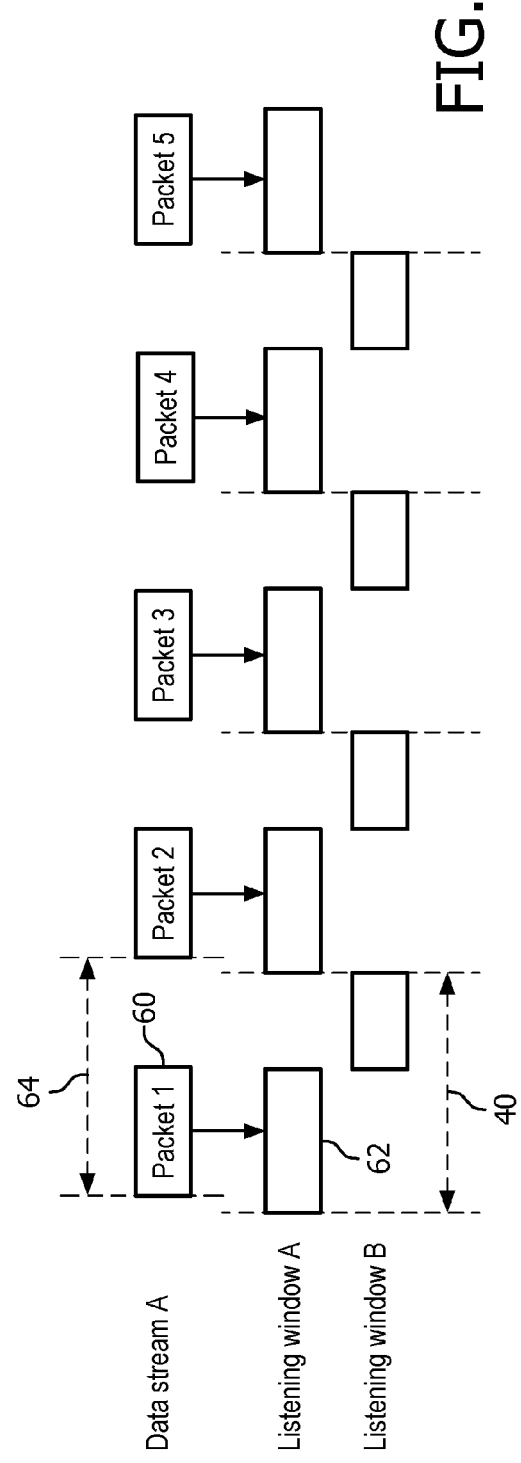

PATIENT MONITORING INVOLVING RECEIVING MULTIPLE ASYNCHRONOUS DATA STREAMS WITH ANTENNA DIVERSITY

CROSS REFERENCE TO RELATED APPLICATIONS

This application is the U.S. National Phase application under 35 U.S.C. §371 of International Application No. PCT/IB2014/063469, filed Jul. 28, 2014, published as WO 2015/022594 on Feb. 19, 2015, which claims the benefit of U.S. Provisional Patent Application No. 61/866,181 filed Aug. 15, 2013. These applications are hereby incorporated by reference herein.

The following relates generally to receiving wireless data transmitted by multiple devices. It finds particular application in conjunction with medical monitoring data received by radio frequency (RF) in RF reflective environments such as a magnetic resonance imaging room, and will be described with particular reference thereto. However, it will be understood that it also finds application in other usage scenarios and is not necessarily limited to the aforementioned application.

Patient monitoring includes medical sensor devices which sense patient vital signs such as electrocardiograms (ECG), blood oxygen saturation ($SpO_2$), respiration, and the like. The devices can transmit the sensed data wirelessly each device using an assigned or predetermined radio-frequency. The data transmitted is sent in data packets transmitted periodically. Each packet typically includes a current sample or patient measurement, and one or more previous measurements. For example, an ECG packet can include a current period waveform data point, and two prior waveform data points. The next ECG packet includes the next waveform data points and repeats the most recent two of the prior packet waveform data points. The data overlap between packets insures against data loss. Each packet, typically of a fixed size includes a checksum to ensure correct receipt of the data. The periodicity of the transmission varies by device.

Typically, a patient monitor uses multiple receivers or radios each receiving the transmitted packets using a separate antenna. Each antenna and receiver pair receives packets only from a single corresponding sensing device. Each sensing device transmits on a separate frequency and is received on a radio dedicated to receiving on the device frequency. As more devices are added, additional radios/antennas are added to the patient monitor. For example, a ECG sensing device transmits on a frequency $F_{ECG}$, and a $SpO_2$ sensing device transmits on a frequency $F_{SpO2}$. The monitor includes one radio receiver dedicated to receiving and demodulating packets transmitted at frequency $F_{ECG}$, and a second radio receiver dedicated to receiving and demodulating packets transmitted at frequency $F_{SpO2}$. Adding a third sensing device adds a third antenna and receiver tuned to a third frequency. The monitor includes a processor which processes the received packets from each radio receiver and typically displays the processed data on a display device.

The performance of the dedicated receivers is diminished by the effects of multipath propagation. For outdoor transmissions, multipath propagation occurs in general when radio waves are reflected by buildings, mountains, the atmosphere, etc. and arrive in multiple paths at a particular radio and interfere with each other. The interference can include destructive interference, e.g. cancel out each other, cause ghosting, and the like. The problem can also exist indoors when RF reflective materials such as the shielding used in structures with strong magnetic fields like magnetic resonance imaging rooms causes reflections.

The following discloses a new and improved multiple asynchronous data streams with antenna diversity which addresses the above referenced issues, and others.

In accordance with one aspect, a radio frequency (RF) receiving apparatus includes a first and second omnidirectional RF antennas at different spatial locations or orientations, a first and second RF receivers, each connected to a corresponding one of the first and second omnidirectional RF antennas, and a processor connected to the first and second RF receivers. The first and second RF receivers receive and demodulate RF signals of at least first and second carrier frequencies to recover data packets from at least a first device which transmits data packets on the first carrier frequency RF signal and a second device which transmits data packets on the second carrier frequency RF signal. The processor is configured to control the RF receivers to cycle between receiving and demodulating the first carrier frequency RF signals concurrently to recover redundant data packets from the first device, and receiving and demodulating the second carrier frequency RF signals concurrently to recover redundant data packets from the second device.

In accordance with another aspect, a method of receiving data packets includes cycling a first and second RF receivers, each connected to a corresponding one of a first and second omnidirectional RF antennas at different spatial locations or orientations, between receiving and demodulating a first carrier frequency RF signals concurrently to recover redundant data packets from at least a first device which transmits data packets on the first carrier frequency RF signal, and receiving and demodulating a second carrier frequency RF signals concurrently to recover redundant data packets from at least a second device which transmits data packets on the second carrier frequency RF signal. The step is performed by an electronic processor.

In accordance with another aspect, a radio frequency (RF) receiving apparatus includes a plurality of RF antennas (20) at different spatial orientations or locations, a plurality of RF receivers, each connected to corresponding one of the omnidirectional RF antennas, and a processor connected to the RF receivers. The RF receivers receive and demodulate RF signals of at least first and second carrier frequencies to recover data packets from a first device which transmits data packets on the first carrier frequency RF signal and a second device which transmits data packets on the second carrier frequency RF signal. The processor is configured to control the RF receivers to cycle between receiving and demodulating the first carrier frequency RF signals concurrently to recover data packets from the first device for a first predetermined time, and receiving and demodulating the second carrier frequency RF signals concurrently to recover data packets from the second device for a second predetermined time.

One advantage is reduction of multipath propagation effects.

Another advantage resides in adding additional transmitting devices without adding additional radios or antennas.

Another advantage resides in the use of existing sensing devices.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a receiver apparatus with multiple asynchronous data streams and antenna diversity in a highly reflective radio frequency (RF) structure.

Figure 2:
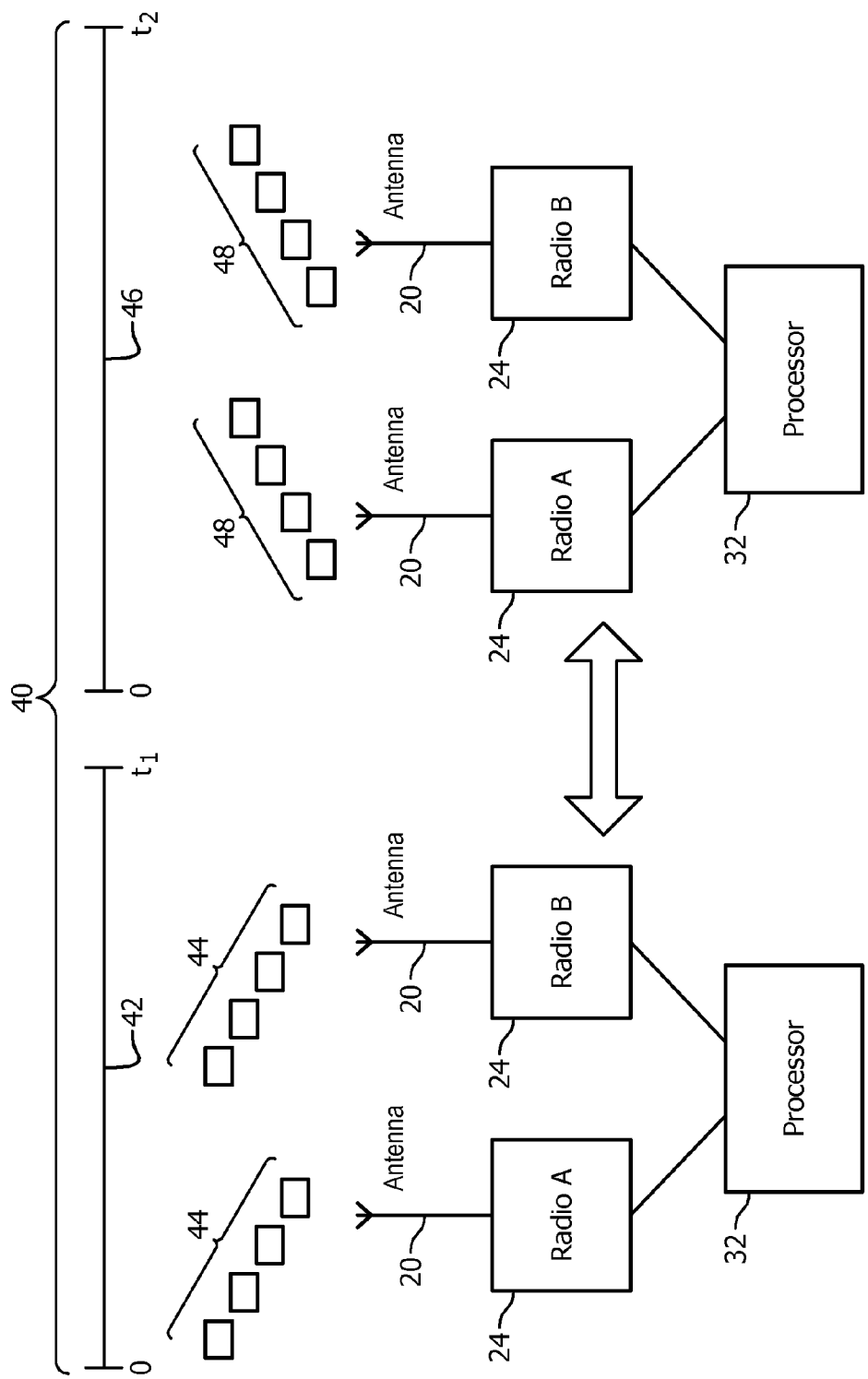

FIG. 2 diagrammatically illustrates an exemplary duty cycle with two transmitting devices.

FIG. 3 diagrammatically illustrates an exemplary acquisition phase.

FIG. 4 diagrammatically illustrates an exemplary acquired phase.

Figure 5:
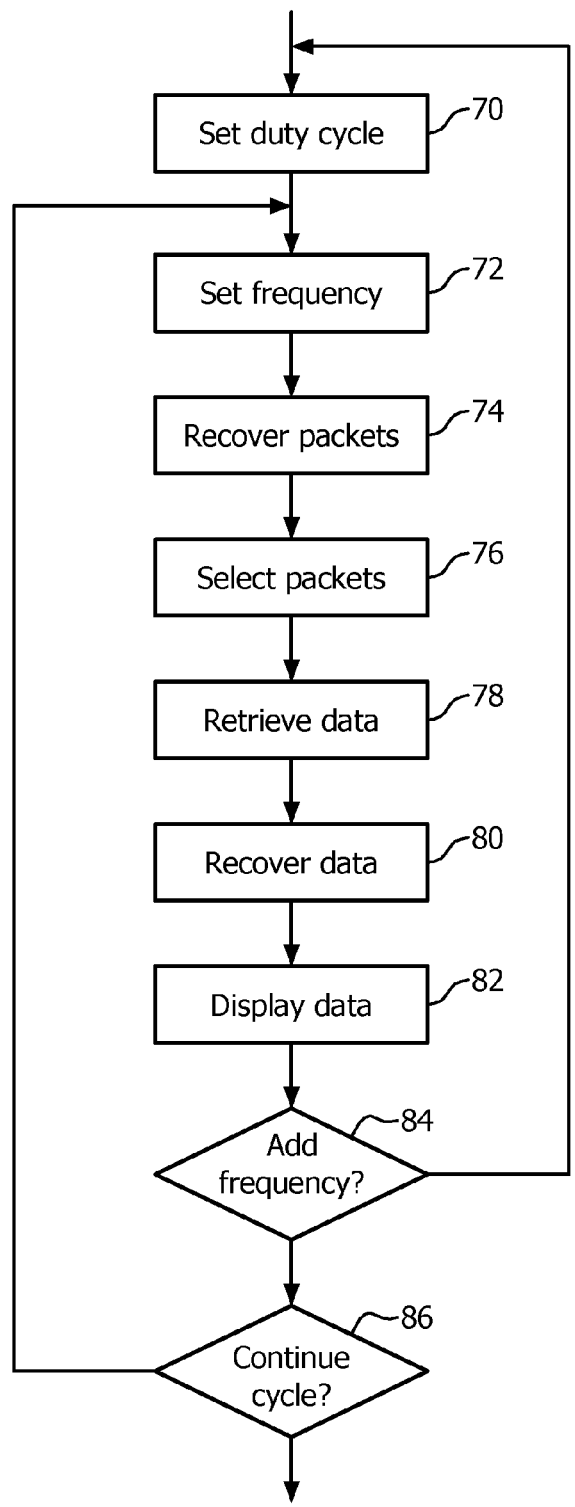

FIG. 5 flowcharts one method of using an embodiment of receiving multiple asynchronous data streams with antenna diversity.

With reference to FIG. 1, an embodiment of a receiver apparatus 10 with multiple asynchronous data streams with antenna diversity in a highly reflective radio frequency (RF) structure 12 is schematically illustrated. An MR scanner 14 is illustrated in partial cross section with a subject 16 being wirelessly monitored. The MR scanner generates a strong magnetic field 18. The structure 12, such as a MR room, in isolating the external RF noise uses materials in the structure, e.g. a copper Faraday cage, which creates a highly reflective RF structure.

The receiver apparatus 10 includes at least two omnidirectional RF antennas 20 with different spatial orientations, e.g. on different sides of the apparatus. The RF antennas 20 receive data packets transmitted by devices 22 such as patient physiological sensors each at a predetermined frequency. Examples of transmitting patient sensors include a $SpO_2$ sensor, an ECG sensor, a respiratory sensor, and the like. The sensors sense patient vital signs, and store the measured vital signs redundantly in a data packet. For example, each packet can contain x prior measurements where x is a redundancy factor such as 3. Each device 22 transmits a data packet at a predetermined interval for that device and at a predetermined frequency. For example, a $SpO_2$ sensor transmits a data packet every 8 milliseconds (ms), while a ECG sensor can transmit a data packet every 1 ms. The data packets which can include measured vital signs are transmitted wirelessly.

A radio or RF receiver 24 is connected to each antenna 20. The receivers 24 receive transmitted data packets. Each receiver receives on the same frequency at the same time. For example using two devices transmitting and two antenna/receiver pairs receiving, both pairs receive on a frequency $F_1$ for a predetermined time $t_1$. Both antenna/receiver pairs switch to a second frequency $F_2$ for a predetermined time $t_2$. A duty cycle includes the sum of the predetermined time periods $\Sigma_1^n t_i$ where n is the number of predetermined periods each at a different frequency. The receivers cycle through each predetermined frequency for each predetermined time period. Data packets are received from each device at a different predetermined frequency. For example, device $D_1$ transmits a packet every 8 ms on a frequency $F_1$, device $D_2$ transmits a packet every one ms on a frequency $F_2$, both devices include a data redundancy factor of 3 in the packets, the antennas receive on the frequency $F_1$ for a first predetermined period, e.g. 1 ms, and then receive on frequency $F_2$ for a second predetermined period, e.g. 7 ms. One packet will be received from $D_1$ in the first predetermined period and one packet from $D_2$ will be missed. Seven packets will be received from $D_2$ in the second predetermined period and none will be missed from $D_1$. The data redundancy factor of 3 in the packet allows data from the missed packet to be reconstructed from either of the next two received packets before data loss occurs. That is, each packet transmits the most recent data, the next most recent data, and the antepenultimate.

A transmitted packet can be reflected and cause destructive interference through multipath propagation to one antenna by arriving via a first path 26 and a second path 28, but another antenna can correctly receive the data packet via a third path 30 because of the spatial separation. When signals arrive at an antenna 180° out of phase, such as by following paths that differ by a half wavelength of the carrier frequency, the signals cancel. Because the antennas are spaced, it is unlikely that destructive interference will occur at both antennas. A processor 32 or a non-software-based controller connected to the receivers 24 is configured to determine correct receipt of the packet by a data integrity checksum or cyclic redundancy check (CRC) included in each packet. Where the same packet is received by both antennas duplicates can be removed by ignoring one of the packets. The processor 32 can be configured to perform the disclosed frequency switching, packet determination, and display construction techniques using a non-transitory storage medium storing instructions (e.g., software) readable by an electronic data processing device such as the processor 32 and executable by the electronic data processing device to perform the disclosed techniques.

A display device 34 is connected to the processor 32. The processor 32 can process or read the data from the packets and display the data on the display device 34. For example, data packets which include ECG waveform, $SpO_2$ values, respiration values and the like can be formatted into a display which superimposes the data in a waveform or other visual format to show each monitored vital sign as a function of time. Alternately or additionally, a display device can be located outside the MR room. As another option, the receivers can be located outside the MR room and be connected to antennas inside the MR room.

With reference to FIG. 2, an exemplary duty cycle 40 with two transmitting devices is diagrammatically illustrated. During a first predetermined period 42 data packets 44 from the first transmitting device $D_1$ are received by both antennas 20. Both receivers 24 are configured to receive and demodulate the carrier frequency $F_1$ of the first transmitting device. The processor 32 checks the received packets based on the checksum to determine that a complete and uncorrupted packet has been received. The processor checks the checksum or CRC of each received packets from each radio and selects the packet with the correct CRC, ignoring duplicate packets. Receiving the same packets on multiple antennas spatially separated provide antenna diversity and increases the likelihood that a packet will be correctly received by at least one antenna.

During a second predetermined period 46, the receivers are reconfigured or switched to receive and demodulate data packets 48 carried by the carrier frequency of the second transmitting device $D_2$ at the second frequency $F_2$. The duty cycle 40 is the total time of all the predetermined periods and the minimal time to switch between frequencies. The duty cycle can be expressed as a time period with allocations to each frequency as a percentage or as the total of the predetermined time periods each expressed as time.

A third device can be added to the duty cycle 40 by allocating a predetermined time period where the receivers are configured to receive on a third frequency transmitted by the third device without an additional receiver or antenna.

The multiplexing of the time between the devices takes advantage of the short duration of packet transmissions, e.g. about 0.5 ms, and the data redundancy within each packet transmission, e.g. repeated data samples, and the relative infrequency of transmission by at least some devices, e.g. transmitting once every duty cycle.

With reference to FIG. 3, an exemplary acquisition phase is diagrammatically illustrated. During the acquisition or synchronization phase, the duty cycle 40 is set different from the maximum interval between transmission period of any device. For example, if one device transmits every 1 ms and another device transmits every 8 ms, then the duty cycle could be set greater than 8 ms such as 8.25 ms as shown, or less than 8 ms such as 7.75 ms. The duty cycle is illustrated with two predetermined periods. During the first predetermined period 42 the frequency matches the transmission of packets from a first device and during the second period 46 the frequency matches the transmission of packets from a second device. Initially a packet 50 transmitted does not line up temporally with the first predetermined period which means that a portion of the packet 50 is not received. However, because the duty cycle is slightly longer than the interval between packet transmissions of the first device, the time of packet transmission will eventually line up with the first predetermined period when the receivers are receiving on that particular frequency and an entire packet 52 will be received. Once the beginning points of the packets are located, the duty cycle of the receivers is synchronized to the transmission duty cycle.

With reference to FIG. 4, an exemplary acquired phase is diagrammatically illustrated. Once packets are received as described in reference to FIG. 3, the processor can synchronize the duty cycle with the transmission cycles of the devices by adjusting the predetermined time periods. The synchronization can include expected drift in the transmission cycles based on measured timing of received packets and/or other known information about the transmitting devices. For example, packets 60 are being received and the first predetermined period 62 is adjusted and/or duty cycle such that the first predetermined period 62 or period when the frequency of the first device is received coincides with the transmission cycle 64 of the packets 60. Each predetermined time period is based on a time interval between packet transmissions for the corresponding device and data redundancy in the data packet. Note that the listening windows are slightly larger than the data packet transmission times. In the above examples with $D_1$ transmitting a 1 ms packet every 1 ms and $D_2$ transmitting a 1 ms packet every 8 ms, the lengthened listening window may result in receiving every packet of $D_2$ but only 6 or every 8 packets from $D_1$. However, with a redundancy factor of 3 all data from $D_1$ is recovered.

FIG. 5 flowcharts one embodied method of receiving data packets in multiple asynchronous data streams with antenna diversity. In a step 70, a duty cycle is set. The duty cycle includes a predetermined period for each transmitting device. Each transmitting device transmits data packets with a different predetermined carrier frequency. The duty cycle is initially set according to the acquiring phase as described in reference to FIG. 3. Each predetermined time period is based on a time period between data packet transmissions for the corresponding device and data redundancy in the data packet. The duty cycle can include a period of time greater than a maximum time period between data packet transmission of each of the devices. For example, if device $D_1$ transmits periodically every X ms, and device $D_2$ transmits periodically every Y ms, then the duty cycle period can be greater than the maximum of X and Y. During each duty cycle period the frequency cycles between each of the carrier frequency RF signals.

In a step 72, the omnidirectional antennas 20 with different spatial orientations each connected to a corresponding one of receivers 24 are controlled by the processor to receive and demodulate data packets on a carrier frequency corresponding to a transmitting device for the predetermined period established with the duty cycle. The receiver/antenna pairs are concurrently set to the same carrier frequency which provides antenna diversity with each predetermined time period. The carrier frequencies $F_1$ and $F_2$ are selected sufficiently close that both antennas are able to pick up $F_1$ and $F_2$.

The processor 32 controls the receivers 24 to concurrently receive and demodulate transmitted packets by the same corresponding device in a step 74. Each receiver receives the transmitted packets which can be affected by multipath propagation, such as a MR suite's Faraday shield structure which reflects RF transmissions.

The processor 32 connected to the receivers 24 selects the received packets in a step 76. The processor verifies transmitted packets from the received packets based on a checksum or CRC. The processor ignores received duplicative packets from the receivers. The step can include synchronizing the duty cycle or adjusting the predetermined time periods based on a timing of the selected packets. The synchronizing during the acquired phase is described in reference to FIG. 4.

In a step 78 the processor retrieves the data from the data packets. The data in the data packets can include electrocardiogram (ECG) waveforms, blood oxygen values ($SpO_2$), respiration, and the like. Missing data is recovered from data packets in a step 80. For example, if a packet is lost due to receiving on a different carrier frequency from the transmitting device, then data can be recovered from the next packet(s) based on the data repeated in the packets.

The retrieved data is displayed on the display device in a step 82. For example, the processor can construct a visual display of the retrieved data values and/or waveform data sequenced in time. The visual display can include any recovered data. The processor can display the constructed visual display on the display device.

In a decision step 84 another carrier frequency and predetermined time period can be added to the duty cycle. For example, a third device $D_3$ transmits on a carrier frequency of $F_3$ for a third predetermined time period. If another frequency, e.g. $F_3$, is added the method returns to the step 70 which sets the duty cycle to include cycling between the previous and added frequencies, e.g. $F_1$ for time period $T_1$, $F_2$ for time period $T_2$, and $F_3$ for time period $T_3$.

In a decision step 86, the continuation of the cycle is determined which returns to the step 72 that sets the next carrier frequency for the receivers, e.g. $F_1$ to $F_2$, $F_2$ to $F_3$, $F_3$ to $F_1$, etc. Each duty cycle includes a repeat of the steps from setting the next carrier frequency for the next predetermined time period for each carrier frequency in the cycle. In one embodiment the constructing and displaying the retrieved data step is deferred according to the number of duty cycles or a predetermined time interval.

The steps are performed by one or more processors such as an electronic processing device. A non-transitory computer-readable storage medium carrying instructions (software) controls the one or more electronic data processing devices to perform the steps.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A radio frequency (RF) receiving apparatus for receiving data from a first medical monitoring sensor which transmits data packets pertaining to a first vital sign with a first periodicity and a second medical monitoring sensor which transmits data packets pertaining to a second vital sign with a second periodicity, the apparatus comprising:
   first and second RF antennas at different spatial locations or orientations;
   first and second RF receivers, each connected to a corresponding one of the first and second RF antennas, and the first and second RF receivers receive and demodulate RF signals of at least first and second carrier frequencies to recover the data packets from the first medical monitoring sensor containing information pertaining to the first vital sign on the first carrier frequency RF signal and to recover the data packets from the second medical monitoring sensor containing information pertaining to the second vital sign on the second carrier frequency RF signal;
   a processor or controller connected to the first and second RF receivers and configured to:
      receive and cycle between the first and the second carrier frequencies such that each carrier frequency is received for predetermined time periods, during an initial acquisition, a total of the cycled predetermined time periods is different from a maximum time interval between data packet transmissions for each of the medical monitoring sensors,
      control the RF receivers to cycle between
         both receivers receiving and demodulating the first carrier frequency RF signals concurrently to recover redundant data packets containing information pertaining to the first vital sign from the first medical monitoring sensor, and
         both receivers receiving and demodulating the second carrier frequency RF signals concurrently to recover redundant data packets containing information pertaining to the second vital sign from the second medical monitoring sensor.

2. A radio frequency (RF) receiving apparatus comprising:
   a first and second RF antennas at different spatial locations or orientations;
   a first and second RF receivers, each connected to a corresponding one of the first and second RF antennas, and the first and second RF receivers receive and demodulate RF signals of at least first and second carrier frequencies to recover data packets from at least a first medical monitoring sensor which transmits data packets containing information pertaining to a first vital sign on the first carrier frequency RF signal and a second medical monitoring sensor which transmits data packets containing information pertaining to a second vital sign on the second carrier frequency RF signal, wherein the first medical monitoring sensor transmits data packets with a first periodicity and the second medical monitoring sensor transmits data packets with a second periodicity;
   a processor or controller connected to the first and second RF receivers and configured to:
      control the RF receivers to cycle between:
         both receivers receiving and demodulating the first carrier frequency RF signals concurrently to recover redundant data packets containing information pertaining to a first vital sign from the first medical monitoring sensor, and
         both receivers receiving and demodulating the second carrier frequency RF signals concurrently to recover redundant data packets containing information pertaining to a second vital sign from the second medical monitoring sensor, and such that each carrier frequency is received for a predetermined time period,
      adjust the predetermined time periods based on a timing of the selected data packets.

3. The apparatus according to claim 1, wherein each predetermined time period is based on a time interval between data packet transmissions for the corresponding medical monitoring sensor and data redundancy in the data packets.

4. The apparatus according to claim 1, wherein the processor is further configured to process the data in the data packets; and further including:
   a display connected to the processor which displays the first and second vital signs.

5. The apparatus according to claim 4, wherein the data packet includes an overlap in the data with at least two prior data packets.

6. The apparatus according to claim 2, wherein the processor is further configured to select between the received data packets concurrently recovered by the first and second receivers based on a checksum or CRC of the received packets.

7. The apparatus according to claim 2, further including a third RF antenna and a third RF receiver configured to receive and demodulate RF signals of a third carrier frequency to recover data packets containing information pertaining to a third vital sign from a third medical monitoring sensor which transmits data packets on the third carrier frequency RF signal, the RF receivers further being configured to cycle between:
   receiving and demodulating the first carrier frequency RF signals concurrently to recover the data packets containing information pertaining to the first vital sign from the first medical monitoring sensor for a first predetermined time, and
   receiving and demodulating the second carrier frequency RF signals concurrently to recover the data packets containing information pertaining to the second vital sign from the second medical monitoring sensor for a second predetermined time; and
   receiving and demodulating the third carrier frequency RF signals concurrently to recover the data packets containing information pertaining to Ran the third vital sign from the third medical monitoring sensor for a third predetermined time,
   wherein the first, second, and third periods of time are not overlapping.

8. A method of receiving data packets, comprising:
   cycling a first and second RF receivers, each connected to a corresponding one of a first and second RF antennas at different spatial locations or orientations, between alternately (a) receiving and demodulating a first carrier frequency RF signals concurrently for a first period of time to recover redundant data packets containing information pertaining to a first vital sign from at least a first medical monitoring sensor which only transmits data packets on the first carrier frequency RF signal, and (b) receiving and demodulating a second carrier frequency RF signals concurrently for a second period of time to recover redundant data packets containing information pertaining to a second vital sign from at least a second medical monitoring sensor which only transmits data packets on the second carrier frequency RF signal, the first and second time periods being not concurrent, wherein the first and second carrier frequencies are different.

9. The method according to claim 8, wherein cycling includes:
   a duty cycle which is different from a maximum time period between data packet transmissions of each of the medical monitoring sensors.

10. The method according to claim 8, further including:
    adjusting the predetermined time periods based on at least one of a timing of the selected data packets and phases of the RF signals.

11. A non-transitory computer-readable storage medium carrying software which controls one or more electronic data processing devices to perform the method according to claim 8.

12. A medical data communication apparatus comprising:
    at least first and second medical monitoring sensor, each configured to sense a vital sign of a subject and to transmit data packets containing information pertaining to the vital sign on the first and second carrier frequency RF signals;
    a receiver system including the first and second receivers each connected to a corresponding one of the first and second RF antennas at different spatial locations or orientations and a computer processor configured to control the first and second receivers to perform the method of claim 8.

13. A method of receiving data packets, comprising:
    cycling a first and second RF receivers with a duty cycle, each connected to a corresponding one of a first and second RF antennas at different spatial locations or orientations, between alternately (a) receiving and demodulating first carrier frequency RF signals concurrently for a first predetermined period of time to recover redundant data packets containing information pertaining to a first vital sign from least a first medical monitoring sensor which transmits data packets on the first carrier frequency RF signal, and (b) receiving and demodulating a second carrier frequency RF signals concurrently for a second predetermined period of time to recover redundant data packets containing information pertaining to a second vital sign from at least a second medical monitoring sensor which transmits data packets on the second carrier frequency RF signal,
    wherein the first and second predetermined time periods are not concurrent, and
    wherein each predetermined time period is based on a time perk between data packet transmissions for the corresponding medical monitoring sensor and data redundancy in the data packet.

* * * * *